(12) United States Patent
Thomson et al.

(10) Patent No.: US 10,631,918 B2
(45) Date of Patent: Apr. 28, 2020

(54) ENERGIZABLE SURGICAL ATTACHMENT FOR A MECHANICAL CLAMP

(71) Applicant: COVIDIEN LP, Mansfield, MA (US)

(72) Inventors: Reid T. Thomson, Erie, CO (US); Grant T. Sims, Boulder, CO (US); Jeffrey R. Townsend, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1017 days.

(21) Appl. No.: 15/156,830

(22) Filed: May 17, 2016

(65) Prior Publication Data

US 2017/0042603 A1 Feb. 16, 2017

Related U.S. Application Data

(60) Provisional application No. 62/205,062, filed on Aug. 14, 2015.

(51) Int. Cl.
*A61B 18/14* (2006.01)
*A61B 18/12* (2006.01)
(Continued)

(52) U.S. Cl.
CPC ........ *A61B 18/1442* (2013.01); *A61B 17/295* (2013.01); *A61B 2017/305* (2013.01);
(Continued)

(58) Field of Classification Search
CPC .......... A61B 2018/00172; A61B 2018/00178; A61B 2017/305; A61B 18/1442;
(Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CN | 2161273 Y | 4/1994 |
| CN | 2688240 Y | 3/2005 |

(Continued)

OTHER PUBLICATIONS

Extended European Search Report issued in corresponding application No. EP 16183956.8 dated Feb. 7, 2017.
(Continued)

*Primary Examiner* — Jaymi E Della
*Assistant Examiner* — Sean W Collins
(74) *Attorney, Agent, or Firm* — Carter, DeLuca & Farrell LLP (57) ABSTRACT

An energizable surgical attachment system is configured for engagement about a mechanical clamp. The energizable surgical attachment includes a clamp sleeve having a first sleeve portion configured to receive a first jaw member of a mechanical clamp and a second sleeve portion configured to receive a second jaw member of a mechanical clamp. Each sleeve portion defines an open proximal end, an enclosed distal end, a lumen extending longitudinally therethrough, and an inner surface. First and second electrically-conductive plates are operably associated with the inner surfaces of the clamp sleeve portions. A connector is coupled to each electrically-conductive plate and a cable management hub is configured to releasably couple the electrosurgical cable with the mechanical clamp.

7 Claims, 6 Drawing Sheets

(51) Int. Cl.
 *A61B 18/00* (2006.01)
 *A61B 17/30* (2006.01)
 *A61B 17/295* (2006.01)

(52) U.S. Cl.
 CPC .............. *A61B 2018/0063* (2013.01); *A61B 2018/00178* (2013.01); *A61B 2018/00577* (2013.01); *A61B 2018/00589* (2013.01); *A61B 2018/00595* (2013.01); *A61B 2018/00601* (2013.01); *A61B 2018/126* (2013.01)

(58) Field of Classification Search
 CPC ........ A61B 2018/00577; A61B 17/295; A61B 2018/0063; A61B 2018/00601; A61B 2018/00595; A61B 2018/00589; A61B 2018/126
 See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,096,864 A | 6/1978 | Kletschka et al. |
| D249,549 S | 9/1978 | Pike |
| 4,120,302 A | 10/1978 | Ziegler |
| 4,165,746 A | 8/1979 | Burgin |
| 4,300,564 A | 11/1981 | Furihata |
| D263,020 S | 2/1982 | Rau, III |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |
| D299,413 S | 1/1989 | DeCarolis |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Kamiyama et al. |
| 5,176,695 A | 1/1993 | Dulebohn |
| 5,190,541 A | 3/1993 | Abele et al. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| D343,453 S | 1/1994 | Noda |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| D348,930 S | 7/1994 | Olson |
| 5,330,471 A | 7/1994 | Eggers |
| D349,341 S | 8/1994 | Lichtman et al. |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| D354,564 S | 1/1995 | Medema |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| D358,887 S | 5/1995 | Feinberg |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |

(56) References Cited

U.S. PATENT DOCUMENTS

| | | |
|---|---|---|
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| D384,413 S | 9/1997 | Zlock et al. |
| 5,662,667 A | 9/1997 | Knodel |
| 5,667,526 A | 9/1997 | Levin |
| 5,674,200 A | 10/1997 | Ruschke et al. |
| 5,681,282 A | 10/1997 | Eggers et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,727,428 A | 3/1998 | LeMaire, III et al. |
| 5,728,121 A | 3/1998 | Bimbo et al. |
| 5,735,848 A | 4/1998 | Yates et al. |
| 5,743,906 A | 4/1998 | Parins |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,779,701 A | 7/1998 | McBrayer et al. |
| H1745 H | 8/1998 | Paraschac |
| 5,792,137 A | 8/1998 | Carr et al. |
| 5,792,177 A | 8/1998 | Kaseda |
| 5,797,938 A | 8/1998 | Paraschac et al. |
| 5,797,958 A | 8/1998 | Yoon |
| 5,800,449 A | 9/1998 | Wales |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| D402,028 S | 12/1998 | Grimm et al. |
| 5,843,080 A | 12/1998 | Fleenor et al. |
| 5,849,022 A | 12/1998 | Sakashita et al. |
| 5,853,412 A | 12/1998 | Mayenberger |
| 5,876,401 A | 3/1999 | Schulze et al. |
| D408,018 S | 4/1999 | McNaughton |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins |
| 5,913,874 A | 6/1999 | Berns et al. |
| 5,921,984 A | 7/1999 | Sutcu et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| D416,089 S | 11/1999 | Barton et al. |
| 5,976,132 A | 11/1999 | Morris |
| 5,989,277 A | 11/1999 | LeMaire, III et al. |
| 6,004,335 A | 12/1999 | Vaitekunas et al. |
| 6,010,516 A | 1/2000 | Hulka |
| 6,024,741 A | 2/2000 | Williamson, IV et al. |
| 6,024,744 A | 2/2000 | Kese et al. |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,031 A | 8/2000 | Mitchell et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| H1904 H | 10/2000 | Yates et al. |
| 6,126,658 A | 10/2000 | Baker |
| 6,152,923 A | 11/2000 | Ryan |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| 6,293,954 B1 | 9/2001 | Fogarty et al. |
| D449,886 S | 10/2001 | Tetzlaff et al. |
| 6,322,561 B1 | 11/2001 | Eggers et al. |
| 6,334,860 B1 | 1/2002 | Dorn |
| 6,334,861 B1 | 1/2002 | Chandler et al. |
| D453,923 S | 2/2002 | Olson |
| 6,350,264 B1 | 2/2002 | Hooven |
| D454,951 S | 3/2002 | Bon |
| 6,352,536 B1 | 3/2002 | Buysse et al. |
| D457,958 S | 5/2002 | Dycus et al. |
| D457,959 S | 5/2002 | Tetzlaff et al. |
| 6,398,779 B1 | 6/2002 | Buysse et al. |
| 6,402,747 B1 | 6/2002 | Lindemann et al. |
| 6,406,485 B1 | 6/2002 | Hossain et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,443,970 B1 | 9/2002 | Schulze et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B2 | 10/2002 | Schmaltz et al. |
| D465,281 S | 11/2002 | Lang |
| D466,209 S | 11/2002 | Bon |

(56) References Cited

U.S. PATENT DOCUMENTS

| | | |
|---|---|---|
| 6,503,248 B1 | 1/2003 | Levine |
| 6,506,189 B1 | 1/2003 | Rittman, III et al. |
| 6,511,480 B1 | 1/2003 | Tetzlaff et al. |
| 6,514,251 B1 | 2/2003 | Ni et al. |
| 6,544,264 B2 | 4/2003 | Levine et al. |
| 6,569,162 B2 | 5/2003 | He |
| 6,585,735 B1 | 7/2003 | Frazier et al. |
| 6,620,161 B2 | 9/2003 | Schulze et al. |
| 6,682,528 B2 | 1/2004 | Frazier et al. |
| 6,685,724 B1 | 2/2004 | Haluck |
| 6,733,498 B2 | 5/2004 | Paton et al. |
| 6,743,229 B2 | 6/2004 | Buysse et al. |
| D493,888 S | 8/2004 | Reschke |
| 6,773,434 B2 | 8/2004 | Ciarrocca |
| D496,997 S | 10/2004 | Dycus et al. |
| D499,181 S | 11/2004 | Dycus et al. |
| D502,994 S | 3/2005 | Blake, III |
| 6,926,716 B2 | 8/2005 | Baker et al. |
| 6,929,644 B2 | 8/2005 | Truckai et al. |
| 6,932,825 B2 | 8/2005 | Anderson |
| D509,297 S | 9/2005 | Wells |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,422,591 B2 | 9/2008 | Phan |
| D582,038 S | 12/2008 | Swoyer et al. |
| 7,632,269 B2 | 12/2009 | Truckai et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,744,623 B2 | 6/2010 | Anderson |
| 7,753,908 B2 | 7/2010 | Swanson |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 8,685,056 B2 | 4/2014 | Evans et al. |
| 2002/0107517 A1 | 8/2002 | Witt et al. |
| 2002/0188294 A1 | 12/2002 | Couture et al. |
| 2003/0018331 A1 | 1/2003 | Dycus et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0199869 A1 | 10/2003 | Johnson et al. |
| 2004/0147925 A1 | 7/2004 | Buysse et al. |
| 2004/0225288 A1 | 11/2004 | Buysse et al. |
| 2004/0236325 A1 | 11/2004 | Tetzlaff et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0101951 A1 | 5/2005 | Wham et al. |
| 2005/0113818 A1 | 5/2005 | Sartor et al. |
| 2007/0244477 A1 | 10/2007 | Santilli et al. |
| 2007/0260241 A1 | 11/2007 | Dalla Betta et al. |
| 2009/0125012 A1 | 5/2009 | Rioux et al. |
| 2010/0087814 A1 | 4/2010 | Desinger et al. |
| 2010/0305567 A1 | 12/2010 | Swanson |
| 2011/0152860 A1* | 6/2011 | Morejohn .......... A61B 18/1442 606/41 |
| 2011/0306972 A1 | 12/2011 | Widenhouse et al. |
| 2013/0018372 A1 | 1/2013 | Sims et al. |
| 2013/0018411 A1 | 1/2013 | Collings et al. |
| 2013/0041370 A1 | 2/2013 | Unger |
| 2013/0046303 A1 | 2/2013 | Evans et al. |
| 2013/0046306 A1 | 2/2013 | Evans et al. |
| 2015/0265305 A1* | 9/2015 | Stulen ................. A61B 17/285 606/169 |

FOREIGN PATENT DOCUMENTS

| | | |
|---|---|---|
| CN | 201267527 Y | 7/2009 |
| EP | 1977707 A1 | 10/2008 |
| WO | 9408524 A1 | 4/1994 |
| WO | 2007-084198 A1 | 7/2007 |

OTHER PUBLICATIONS

Notification of the First Office Action issued in corresponding Chinese office action dated Aug. 23, 2018, with English translation, 10 pages.

* cited by examiner

ENERGIZABLE SURGICAL ATTACHMENT FOR A MECHANICAL CLAMP

CROSS REFERENCE TO RELATED APPLICATION

The present application claims the benefit of and priority to U.S. Provisional Application Ser. No. 62/205,062, filed on Aug. 14, 2015, the entire contents of which are incorporated herein by reference.

BACKGROUND

Technical Field

The present disclosure relates to surgical devices and, more specifically, to an energizable surgical attachment for converting a mechanical clamp into a bipolar forceps for treating, e.g., sealing, cauterizing, coagulating/desiccating, tissue and/or for energy-based tissue cutting.

Background of Related Art

A hemostat or forceps is a plier-like tool which uses mechanical action between its jaws to constrict tissue. Electrosurgical forceps utilize both mechanical clamping action and electrical energy to affect hemostasis by heating tissue to treat, e.g., coagulate, cauterize, cut and/or seal tissue. By utilizing an electrosurgical forceps, a surgeon can treat tissue in a desired manner by controlling the intensity, frequency and duration of the electrosurgical energy applied to tissue. Generally, the electrical configuration of electrosurgical forceps can be categorized in two classifications: monopolar electrosurgical forceps and bipolar electrosurgical forceps.

SUMMARY

Various types of mechanical clamps are available that provide mechanical clamping action without the ability to supply electrosurgical energy. It would therefore be advantageous to provide an energizable surgical attachment for use with any or all of these mechanical clamps to convert the mechanical clamp into an electrosurgical forceps capable of both mechanically clamping tissue and treating tissue with electrosurgical energy. These and other aspects and features of the present disclosure are detailed below, wherein the term "distal" refers to the portion that is being described which is further from a user, while the term "proximal" refers to the portion that is being described which is closer to a user. Further, to the extent consistent, any of the aspects and features described herein may be used in conjunction with any or all of the other aspects and features described herein.

In accordance with the present disclosure, an energizable surgical attachment configured for engagement about a mechanical clamp, is provided. The attachment includes a clamp sleeve having a first sleeve portion configured to receive a first jaw member of a mechanical clamp and a second sleeve portion configured to receive a second jaw member of a mechanical clamp. Each sleeve portion defines an open proximal end, an enclosed distal end, a lumen extending longitudinally therethrough, and an inner surface. A first electrically-conductive plate is operably associated with the opposed inner surface of the first sleeve portion. A second electrically-conductive plate is operably associated with the opposed inner surface of the second sleeve portion.

An electrosurgical cable is also provided as is a connector coupling the electrosurgical cable to each of the first and second electrically-conductive plates. A cable management hub is disposed about the electrosurgical cable and configured to releasably couple to a mechanical clamp.

In an aspect of the present disclosure, the clamp sleeve is made of a flexible material to facilitate reception of the first and second jaw members of the mechanical clamp.

In another aspect of the present disclosure, at least one of the first and second electrically-conductive plates defines a sinuous configuration to facilitate flexing.

In yet another aspect of the present disclosure, the first electrically-conductive plate and the second electrically-conductive plate are configured to conduct energy therebetween to treat tissue grasped between the first and second sleeve portions.

In still another aspect of the present disclosure, the first and second sleeve portions of the clamp sleeve are configured to receive jaw members having various different configurations.

In still yet another aspect of the present disclosure, the first electrically-conductive plate is housed on the inside of the inner surface of the first sleeve portion, and the second electrically-conductive plate is housed on the inside of the inner surface of the second sleeve portion.

In another aspect of the present disclosure, the first electrically-conductive plate is housed on the outside of the inner surface of the first sleeve portion, and the second electrically-conductive plate is housed on the outside of the inner surface of the second sleeve portion.

Also provided in accordance with the present disclosure is a surgical system including a mechanical clamp and an energizable surgical attachment. The mechanical clamp includes first and second handle portions and first and second jaw members extending distally from the respective first and second handle portions. The energizable surgical attachment includes a clamp sleeve including a first sleeve portion configured to receive the first jaw member of the mechanical clamp and a second sleeve portion configured to receive the second jaw member of the mechanical clamp. Each sleeve portion defines an open proximal end, an enclosed distal end, a lumen extending longitudinally therethrough, and an inner surface. The energizable surgical attachment further includes a first electrically-conductive plate operably associated with the inner surface of the first sleeve portion and a second electrically-conductive plate operably associated with the inner surface of the second sleeve portion. An electrosurgical cable includes a connector coupling the electrosurgical cable to each of the first and second electrically-conductive plates. A cable management hub is disposed about the electrosurgical cable and releasably couples the electrosurgical cable to a proximal end of a mechanical clamp.

The energizable surgical attachment and/or mechanical clamp may further include any of the aspects and features detailed above or otherwise herein.

Provided in accordance with the present disclosure is another energizable surgical attachment configured for engagement about a mechanical clamp. The attachment includes a clamp sleeve including a first sleeve portion configured to receive a first jaw member of a mechanical clamp and a second sleeve portion configured to receive a second jaw member of a mechanical clamp. Each sleeve portion defines an open proximal end, an enclosed distal end, a lumen extending longitudinally therethrough, and an inner surface. The clamp sleeve is made of a flexible material to facilitate reception of the first and second jaw members of a mechanical clamp. A first electrically-conductive plate is operably associated with the inner surface of the first sleeve portion and a second electrically-conductive plate is operably associated with the inner surface of the second sleeve portion. The first and/or second electrically-conductive plate defines a sinuous configuration to facilitate flexing.

BRIEF DESCRIPTION OF THE DRAWINGS

Various aspects and features of the present disclosure are described herein with reference to the drawings wherein.

DETAILED DESCRIPTION

Turning to FIGS. 1A-2B, an energizable surgical attachment 100 provided in accordance with the present disclosure is shown configured for use with any suitable mechanical clamp to facilitate treating and/or cutting tissue. Although energizable surgical attachment 100 is described and illustrated herein in use in conjunction with mechanical clamp 410, energizable surgical attachment 100 is equally applicable for use with any other suitable mechanical clamp, e.g., mechanical clamp 420 (FIG. 4A) or mechanical clamp 430 (FIG. 4B) to facilitate treating tissue. Further, to the extent consistent, any of the embodiments detailed herein below, although described separately, may include any or all of the features of any or all of the other embodiments of the present disclosure.

Figure 1A:
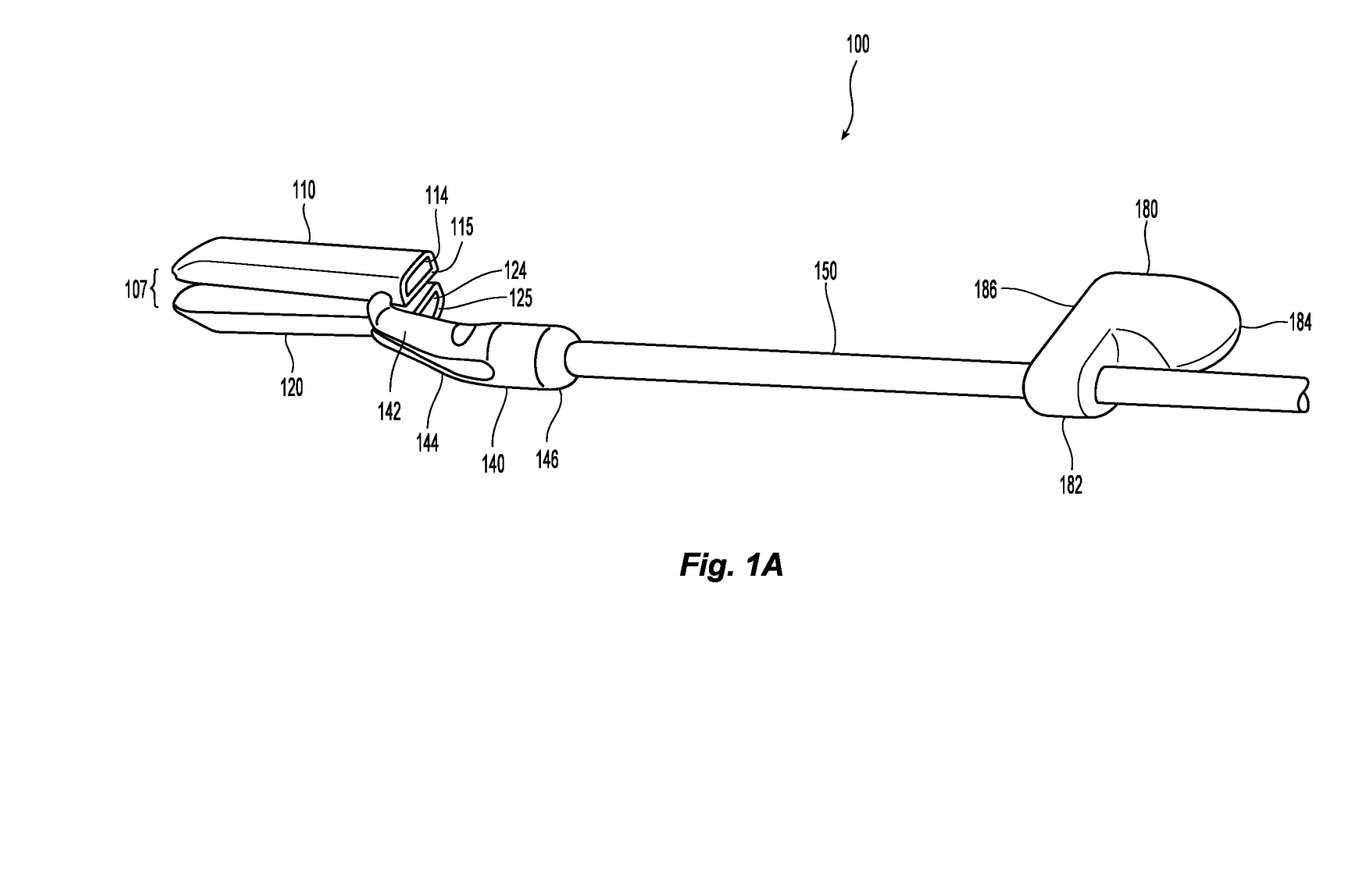
FIG. 1A is a side, perspective view of a energizable surgical attachment provided in accordance with the present disclosure and disposed in an open position.
Figure 1B:
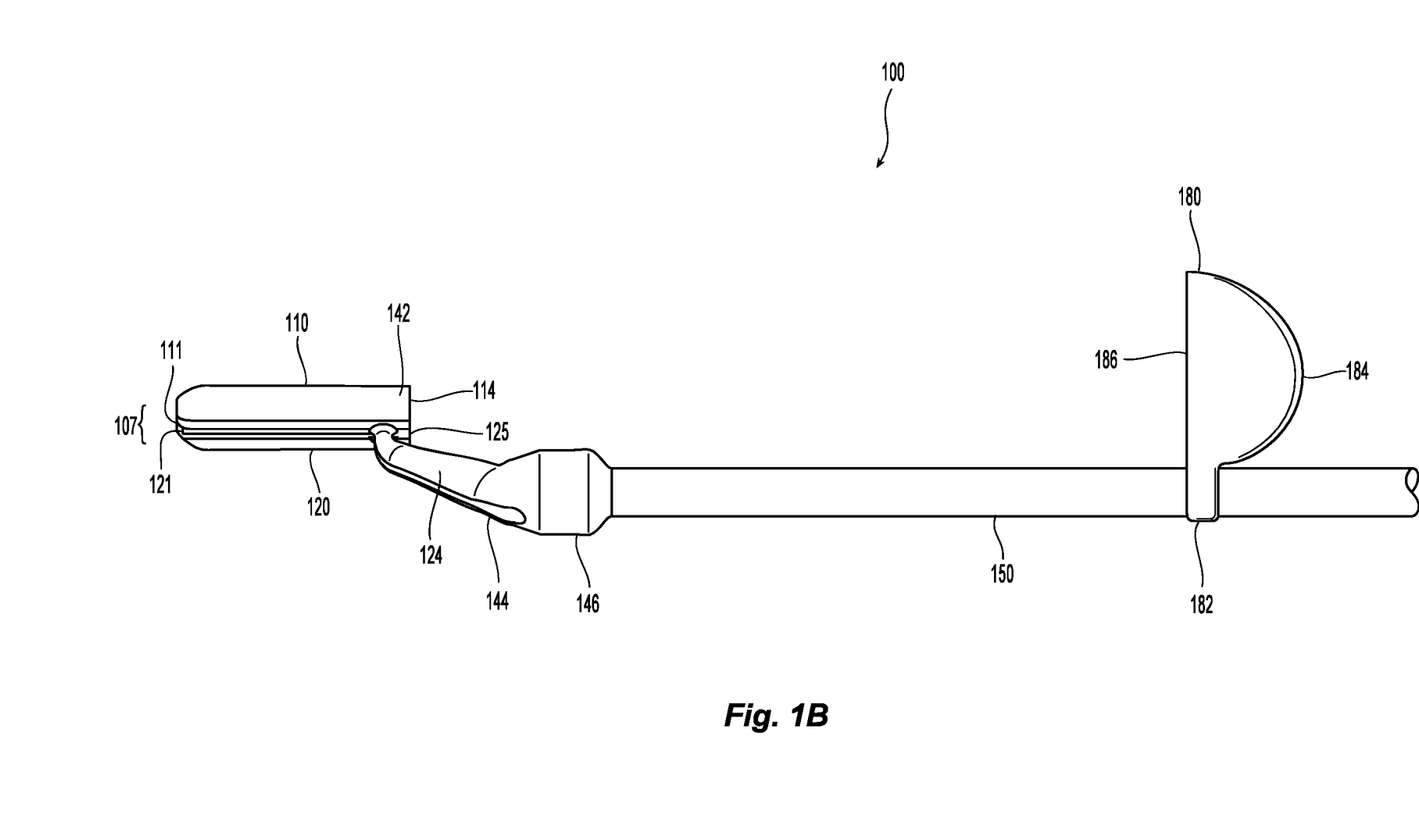
FIG. 1B is a side, perspective view of the energizable surgical attachment of FIG. 1A, disposed in a closed position.
Figure 2A:
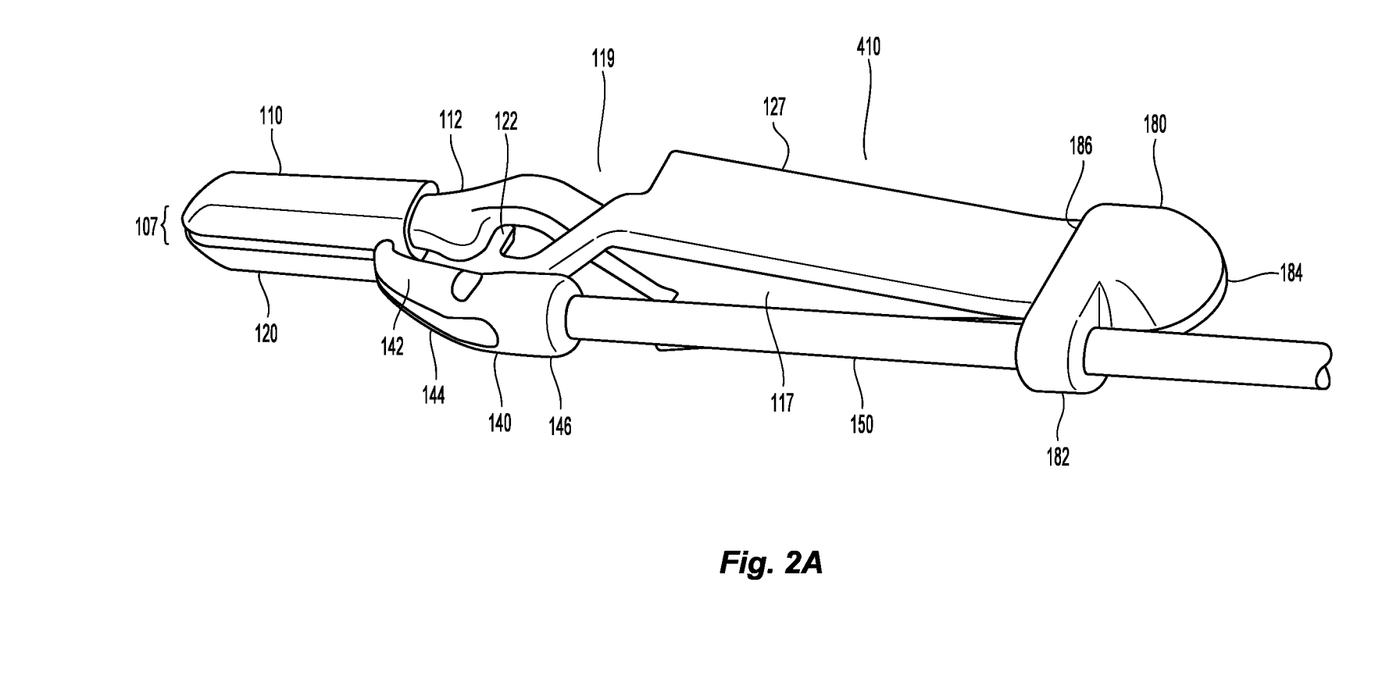
FIG. 2A is a perspective view of the energizable surgical attachment of FIG. 1A engaged with a bulldog clamp.
Figure 2B:
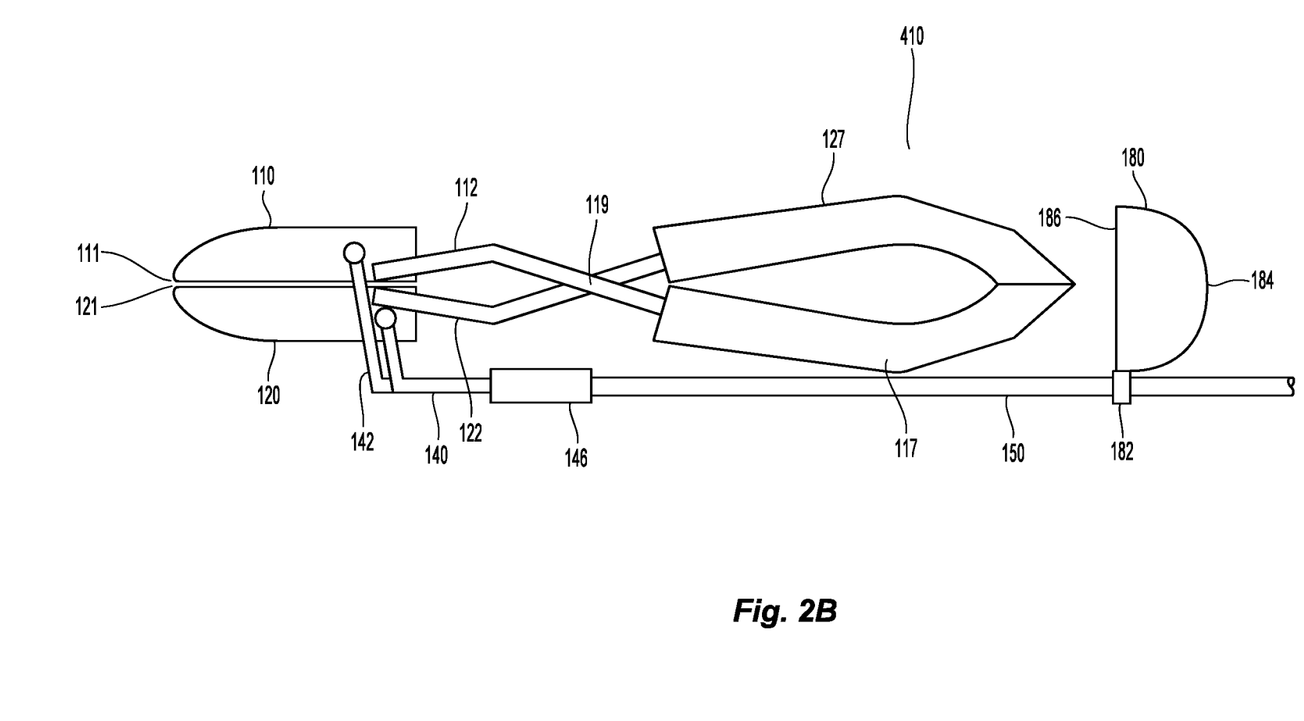
FIG. 2B is a side, schematic view of the energizable surgical attachment of FIG. 1A illustrating engagement thereof with the bulldog clamp of FIG. 2A.

Referring to FIGS. 2A and 2B, mechanical clamp 410 is shown including energizable surgical attachment 100 engaged thereabout. Mechanical clamp 410, also known as a "bulldog" clamp generally includes a first jaw member 112 that curves downward and slopes upwards forming a first handle portion 117 and a second jaw member 122 which curves downward and slopes upwards forming a second handle portion 127. The first and second handle portions 117, 127 are connected at their proximal ends via hinge coupling 119 and are biased apart from one another corresponding to a closed position of the first and second jaw members 112, 122 wherein the first and second jaw members 112, 122 are approximated relative to one another. The jaw members 112 and 122 of mechanical clamp 410 maintain this closed position until a force is applied to the handle portions 117, 127 sufficiently so as to urge handle portions 117, 127 towards one another, thereby moving jaw members 112, 122 to an open position, wherein first and second jaw members 112, 122 are spaced-apart from one another.

Referring to FIGS. 1A-3, energizable surgical attachment 100 generally includes a clamp sleeve 107 having a first sleeve portion 110 and a second sleeve portion 120. First and second sleeve portions 110, 120 define opposed first and second inner surfaces 115, 125 (FIG. 1A), respectively. Energizable surgical attachment 100 further includes a connector 140 extending proximally from clamp sleeve 107, an electrosurgical cable 150 coupled to clamp sleeve 107 via connector 140, and a cable management hub 180 configured to inhibit tangling of electrosurgical cable 150. As detailed below, clamp sleeve 107 of energizable surgical attachment 100 is configured for positioning about jaw members 112, 122 (FIGS. 2A-2B) of mechanical clamp 410 (FIGS. 2A-2B), or other suitable mechanical clamp, for use therewith in treating tissue.

Figure 4A:
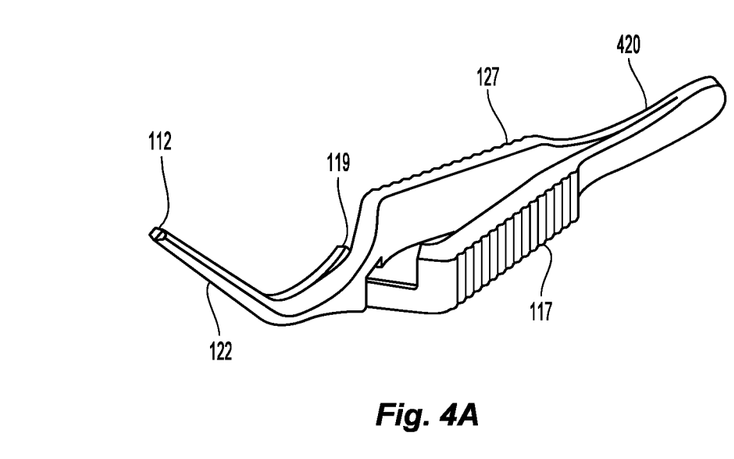
FIGS. 4A and 4B illustrate examples of other mechanical clamps with which the energizable surgical attachment of FIG. 1A may be used.
Figure 4B:
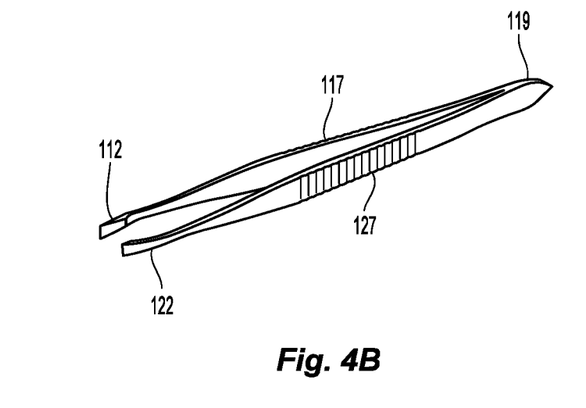

As noted above, first sleeve portion 110 and second sleeve portion 120 each define an inner surface 115, 125, respectively. First sleeve portion 110 and second sleeve portion 120 each also define an elongated configuration and have interior lumens 114, 124, respectively, that are open at the respective proximal ends thereof and enclosed at the respective distal ends thereof. First and second interior lumens 114, 124, respectively, are configured to receive jaw members 112, 122, respectively, of mechanical clamp 410 therein such that movement of jaw members 112, 122 of mechanical clamp 410 between the open position and the closed position effects movement of first and second inner surfaces 115, 125 relative to one another between a spaced-apart position (FIG. 1A) and an approximated position (FIG. 1B) for grasping tissue therebetween. First and second sleeve portions 110, 120 may be formed from or coated with an electrically-insulative material and each may be formed from a flexible material, e.g., silicone, to facilitate friction-fit engagement about the respective jaw members 112, 122 (FIGS. 2A and 2B) of mechanical clamp 410 (FIGS. 2A and 2B) and/or to permit sleeve portions 110, 120 to flex and/or contour to accept the jaw members of various different mechanical clamps, e.g., mechanical clamps having various different sized jaws members, curved and/or angled jaw members, etc., such as mechanical clamps 420, 430 (FIGS. 4A and 4B).

Figure 3:
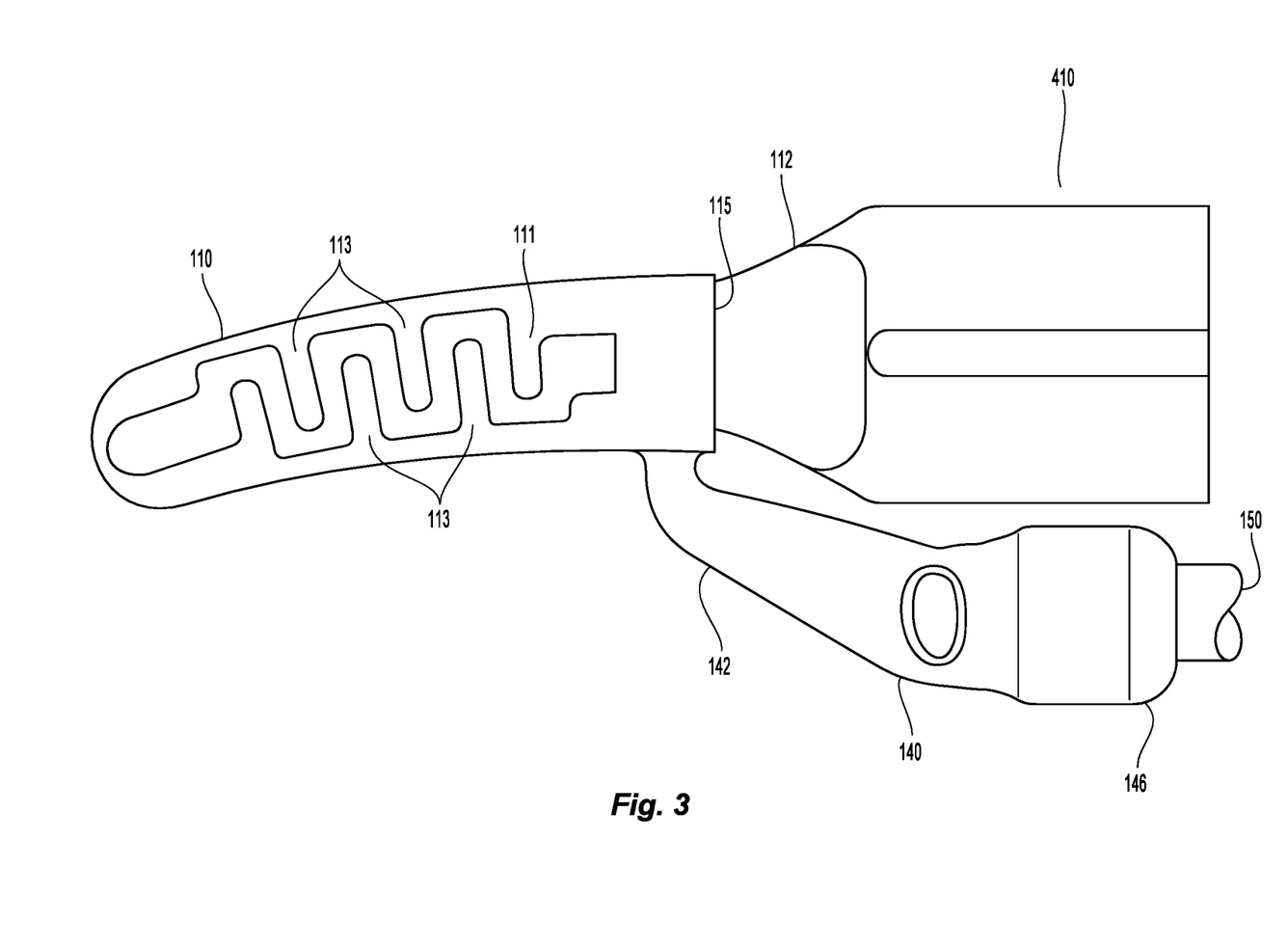
FIG. 3 is a top view of the distal end of the energizable surgical attachment of FIG. 1A engaged with the bulldog clamp of FIG. 2A.

With particular reference to FIG. 3, each sleeve portion 110, 120 further includes an electrically-conductive tissue-treating plate 111 (only plate 111 of sleeve portion 110 is shown; the plate of sleeve portion 120 is substantially similar and, thus, not shown and described herein). Electrically-conductive tissue-treating plate 111 is embedded within the inner surface 115 of sleeve portion 110 or disposed on the exterior of inner surface 115. In one embodiment, electrically-conductive tissue-treating plate 111 defines a sinuous or serpentine-shaped configuration extending longitudinally along sleeve portion 110. Alternatively, electrically-conductive tissue-treating plate 111 can be configured to define other suitable configurations which allow flexing along sleeve portion 110. This configuration permits electrically-conductive tissue-treating plate 111 to flex along with the first sleeve portion 110 once the corresponding jaw member of the mechanical clamp 410 has been inserted into first interior lumen 114. In particular, electrically-conductive tissue-treating plate 111 defines valley areas 113 which are able to increase and decrease in size as electrically-conductive tissue-treating plate 111 and sleeve portion 110 flex and/or contour to the particular shape of the jaw member of the mechanical clamp used therewith. As such, sleeve portion 110 and electrically-conductive tissue-treating plate 111 allow energizable surgical attachment 100 to be used with various different mechanical clamps, e.g., mechanical clamps having various different sized jaws members, curved and/or angled jaw members, etc., such as mechanical clamps 420, 430 (FIGS. 4A and 4B). In one embodiment, the electrically-conductive tissue-treating plate (not shown) associated with inner surface 125 of sleeve portion 120 mirrors the configuration of plate 111.

Referring again to FIGS. 1A-3, connector 140 defines a bifurcated distal end having first and second portions 142, 144, respectively, that are attached to the respective first and second sleeve portions 110, 120. Connector 140 further defines a proximal hub 146 configured to receive the distal end of electrosurgical cable 150. Connector 140 is configured to permit passage of electrode leads (not explicitly shown) housed within electrosurgical cable 150 through connector 140 for coupling with respective tissue-treating plates 111, (not shown) of first and second sleeve portions 110, 120, respectively, such that electrosurgical energy may be delivered from electrosurgical cable 150 to tissue-treating plates 111, (not shown), respectively, to treat tissue grasped between first and second sleeve portions 110, 120. Electrosurgical cable 150, at its proximal end, includes an electrosurgical plug (not shown) to enable connection to an electrosurgical generator (not shown) or other suitable energy source.

Cable management hub 180 includes a collar 182 and a base 184. Collar 182 is disposed about electrosurgical cable 150 and is able to both slide along the length of electrosurgical cable 150 and rotate about electrosurgical cable 150. Base 184 of cable management hub 180 defines a slot 186 configured to releaseably receive hinge coupling 119 of mechanical clamp 410 without impeding the operation thereof. Cable management hub 180 may be configured and/or sized differently depending on the type of mechanical clamp 410, 420 or 430 (FIGS. 4A, 4B, or 4C) used with energizable surgical attachment 100 and may be removably coupled about electrosurgical cable 150 to permit use of various different cable management hubs 180. For example, when the mechanical clamp 430 of FIG.4 C is used, a cable management hub 180 may be provided with an elongated configuration as compared to the cable management attachment 180 utilized with mechanical clamp 410 of FIG. 4A. It is envisioned that collar 182 define a "C"-shaped configuration having an expandable mouth (not shown) defined within collar 182, or may otherwise be configured to permit engagement of various different cable management hubs 180 about electrosurgical cable 150, e.g., depending upon the particular configuration of the mechanical clamp used therewith.

Referring now to FIGS. 4A and 4B, various other non-exhaustive examples of mechanical clamps which may be used with energizable surgical attachment 100 are shown. The mechanical clamps used may range from and are not limited to straight bulldog clamps (FIGS. 2A-2B), curved bulldog clamps (FIG. 4A), straight tweezers (FIG. 4C), curved tweezers (not shown), etc.

The mechanical clamp 420 of FIG. 4B possesses straight jaw members 112 and 122. Similar to mechanical clamp 410 (FIGS. 2A-2B), the jaw members 112 and 122 of mechanical clamp 420 maintain a closed position until a force is applied to the first handle portion 117 and the second handle portion 127. Once the force is applied to the first handle portion 117 and the second handle portion 127, jaw members 112 and 122 are moved to an open position.

The mechanical clamp 430 of FIG. 4C also possesses straight jaw members 112 and 122. However, unlike mechanical clamps 410 and 420 (FIG. 4A and FIG. 4B), mechanical clamp 430 maintains an open position until a force is applied to the first handle portion 117 and the second handle portion 127. Once the force is applied to the first handle portion 117 and the second handle portion 127, jaw members 112 and 122 are moved to a closed position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An energizable surgical attachment configured for engagement about a mechanical clamp, comprising:
    a clamp sleeve including a first sleeve portion configured to receive a first jaw member of the mechanical clamp and a second sleeve portion configured to receive a second jaw member of the mechanical clamp, each of the first sleeve portion and the second sleeve portion defining an open proximal end, an enclosed distal end, a lumen extending longitudinally therethrough, and an inner surface;
    a first electrically-conductive plate operably associated with the inner surface of the first sleeve portion;
    a second electrically-conductive plate operably associated with the inner surface of the second sleeve portion;
    an electrosurgical cable;
    a connector configured to couple the electrosurgical cable to each of the first and second electrically-conductive plates, the connector including a bifurcated distal end portion having a first portion coupled to the first sleeve portion and a second portion coupled to the second sleeve portion, the bifurcated distal end portion configured to move between an expanded state and a contracted state as the first and second jaw members of the mechanical clamp move between an open position and a closed position; and
    a cable management hub disposed about the electrosurgical cable and configured to releasably couple to the mechanical clamp.

2. The energizable surgical attachment according to claim 1, wherein the clamp sleeve is made of a flexible material to facilitate reception of the first and second jaw members of the mechanical clamp.

3. The energizable surgical attachment according to claim 2, wherein at least one of the first or second electrically-conductive plates defines a sinuous configuration to facilitate flexing.

4. The energizable surgical attachment according to claim 1, wherein the first electrically-conductive plate and the second electrically-conductive plate are configured to conduct energy therebetween to treat tissue grasped between the first and second sleeve portions.

5. The energizable surgical attachment according to claim 1, wherein the first and second sleeve portions of the clamp sleeve are configured to receive jaw members having various different configurations.

6. The energizable surgical attachment according to claim 3, wherein the first electrically-conductive plate is housed on an inside of the inner surface of the first sleeve portion, and
    wherein the second electrically-conductive plate is housed on an inside of the inner surface of the second sleeve portion.

7. The energizable surgical attachment according to claim 3, wherein the first electrically-conductive plate is housed on an outside of the inner surface of the first sleeve portion, and wherein the second electrically-conductive plate is housed on an outside of the inner surface of the second sleeve portion.

* * * * *